Figure 3:
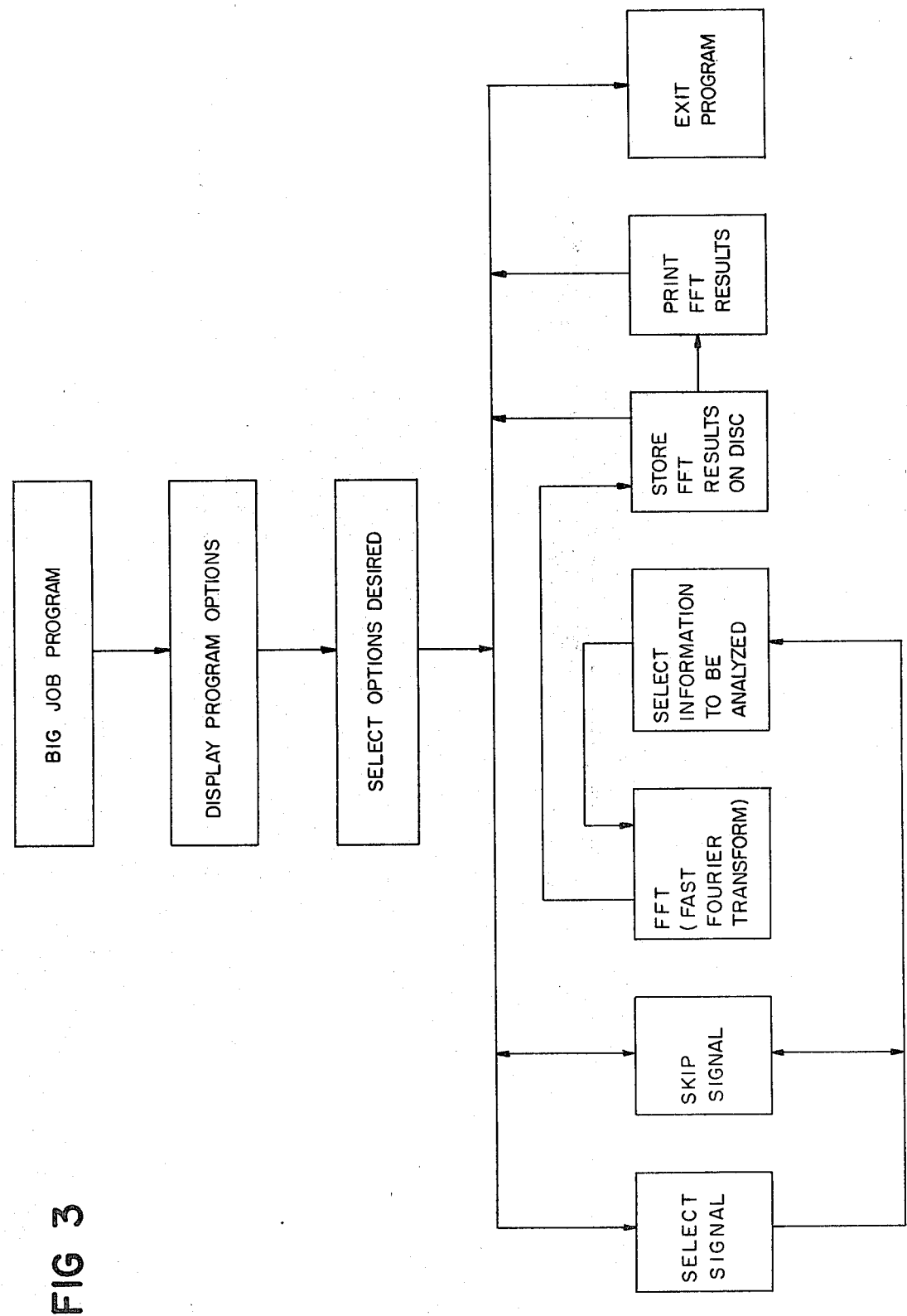

United States Patent [19]

Abts et al.

[11] 4,339,944
[45] Jul. 20, 1982

[54] ULTRASONIC PARTICULATE IDENTIFICATION

[75] Inventors: Leigh R. Abts, Providence; Robert T. Beyer, East Providence, both of R.I.

[73] Assignee: Micro Pure Systems, Inc., Smithfield, R.I.

[21] Appl. No.: 151,834

[22] Filed: May 21, 1980

[51] Int. Cl.$^3$ ............................................. G01N 29/02
[52] U.S. Cl. ........................................ 73/19; 73/61 R
[58] Field of Search ................. 73/19, 61 R, 602, 629, 73/659, 632

[56] References Cited

U.S. PATENT DOCUMENTS 3,553,636 1/1971 Baird .................................. 73/61 R
4,217,909 8/1980 Papadofrangakis et al. ......... 73/602

OTHER PUBLICATIONS

Abts et al., "Computerized Discrimination of Microemboli in Extracorporreal Circuits", *The American Journal of Surgery*, pp. 535–538, Apr. 1978.

Hickling, "Analysis of Echos From a Solid Elastic Sphere in Water", *Journal of the Acoustical Society of America*, vol. 34, No. 10, pp. 1582–1592, Oct. 1962.

Jacobson et al., "Ultrasonic Detection of Bloodstream Emboli", *Ocean '73 IEEE International Conference on Engineering in Ocean Envir.*, pp. 141–147, Sep. 1973.

Lubbers et al., "An Ultrasonic Detector for Microgasemboli in a Bloodflow Line", *Ultrasound in Med. and Biol.*, vol. 2, No. 4, pp. 301–310, 1977.

*Primary Examiner*—Stephen A. Kreitman

[57] ABSTRACT

A method of identifying discontinuities in a flow by transforming an ultrasonic pulse reflected from an unknown discontinuity into a frequency spectrum and comparing that spectrum with the spectra of known discontinuities.

7 Claims, 7 Drawing Figures

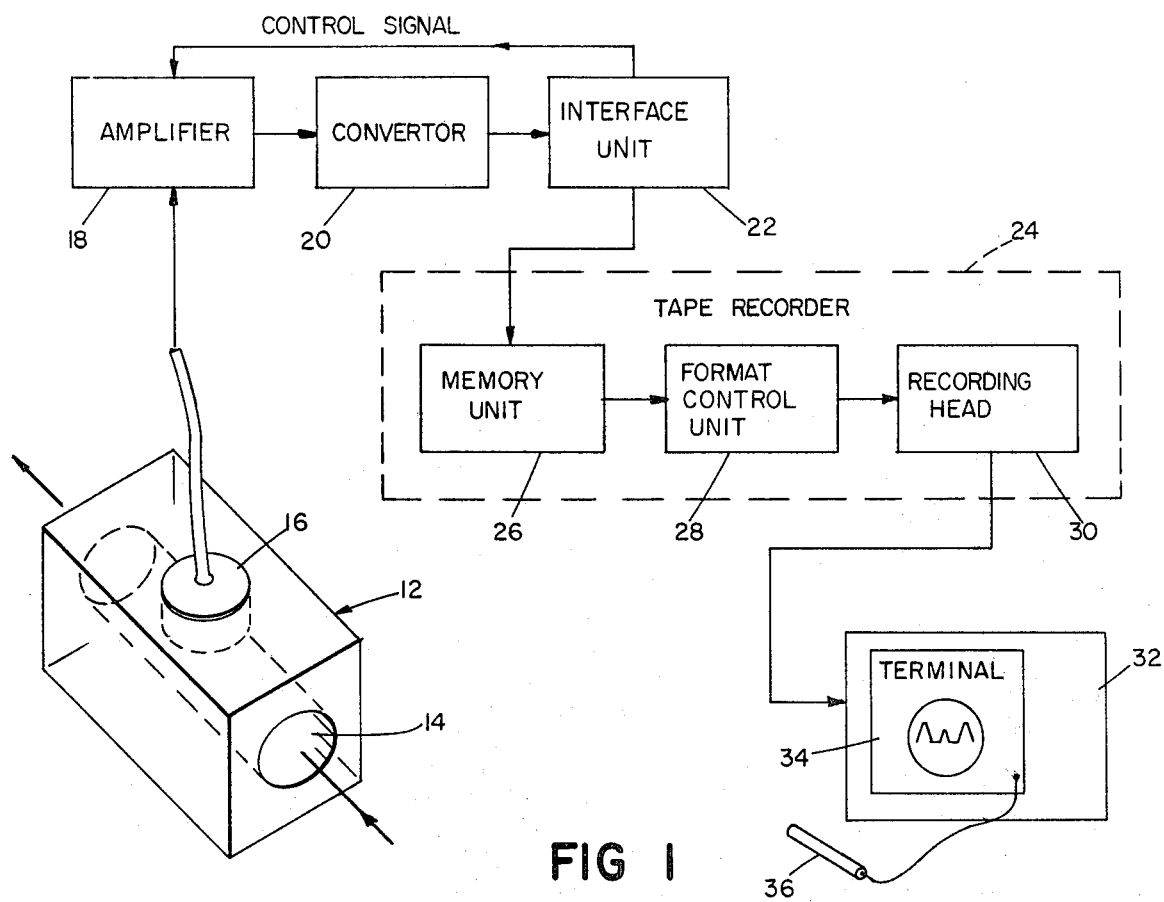
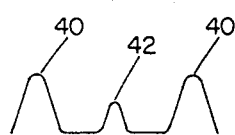
FIG 2a
FIG 2b
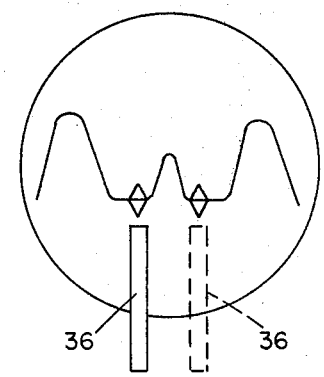
FIG 2c
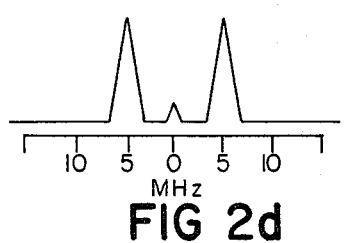
FIG 2d
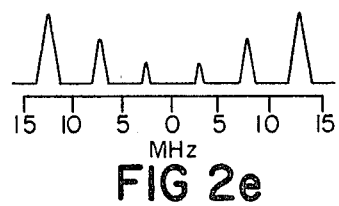
FIG 2e

ULTRASONIC PARTICULATE IDENTIFICATION

FIELD OF THE INVENTION

This invention relates to identifying unknown discontinuities in flowing fluid streams.

BACKGROUND OF THE INVENTION

It is possible to detect small discontinuities in a flow. Apparatus for such detection is fully set forth in Abts U.S. Pat. No. 4,112,773, Abts U.S. Pat. No. 4,214,484, and Abts U.S. Pat. No. 4,217,781, all hereby incorporated by reference.

In addition, it may also be desirable to identify the type of discontinuity. It is known that ultrasonic reflections from large solid objects have some different characteristics.

SUMMARY OF THE INVENTION

We have discovered that different discontinuities in flowing fluids can be identified by creating a frequency spectrum from an ultrasonic signal reflected by an unknown discontinuity in the flow and comparing that spectrum with the spectra of known discontinuities. In preferred embodiments, a returning signal from an unknown discontinuity is converted into a digital word, and the portion of the word representing the unknown discontinuity is converted into a frequency spectrum by a fast Fourier transform. The frequency spectrum is then displayed.

PREFERRED EMBODIMENT

We turn now to the structure and operation of a preferred embodiment, after first briefly describing the drawings.

DRAWINGS

FIG. 1 is a partial block diagram of a discontinuity identification system;

FIGS. 2a–e are various signal waveforms;

FIG. 3 is a flow diagram of the computer program of this invention.

STRUCTURE

Referring to FIG. 1, there is shown a discontinuity identification system. The system has a flow chamber 12 with a bore 14 extending therethrough. Ultrasonic transmitter-receiver 16 is mounted on chamber 12 so as to direct pulses of ultrasonic energy across the bore 14. Chamber and transmitter-receiver are described in Abts U.S. Pat. No. 4,112,773 and in Abts U.S. Pat. No. 4,214,484 and U.S. Pat. No. 4,217,781.

Transmitter-receiver 16 is electrically connected to an amplifier 18, an MCM 1100 monitor, which is available from Micro Pure Systems Inc., the assignee hereof. The output signal from amplifier 18 is fed to an input of a 100 MH$_z$ analog-to-digital converter 20 (Biomation 8100 Transit Recorder). Converter 20 is connected through an interface unit 22 (Dynetech Magnetic Tape Interface) to a magnetic tape recorder 24. Recorder 24 has, as pre-stages, a buffer memory unit 26 and a format control unit 28. The output signal from the interface unit 22 is sent to the buffer memory unit 26, which in turn feeds a signal to the format control unit 28. The output of format control unit 28 is sent to a magnetic tape recording head 30. Recorder 24 may be a Kennedy Model 9300 tape recorder. A Kennedy Model 9217B buffer memory and a Kennedy Model 9218 format control unit are suitable as the pre-stages.

Computer 32 is configured to read magnetic tape from recorder 24. Computer 32 has a visual graphics terminal 34 with a light pen 36. A PDP 11/40 Computer with a VT Graphics Terminal are suitable.

OPERATION

A flow containing unknown discontinuities passes through bore 14 of chamber 12. The discontinuities may be as small as 1–2 microns in diameter. The transmitter-receiver 16 transmits a series of ultrasonic pulses into the bore and across the flow and receives the reflected pulses, as explained in detail in Abts U.S. Pat. No. 4,112,773 and Abts U.S. Pat. Nos. 4,214,484 and 4,217,781. A reflected pulse signal is shown in FIG. 2a. The large end peaks 40 are caused by the reflection of the ultrasonic pulse from the near and far walls of the bore 14. Central peak 42 represents a reflection from a discontinuity in the flow. This reflected signal is sent to the amplifier 18.

Amplifier 18 amplifies the signal of FIG. 2a and sends the amplified signal to the analog-to-digital converter 20. Converter 20 changes the signal to a digital one. For this conversion, the analog signal is sampled at 2,048 successive locations along its x axis. Each sampling generates a data point at one of 256 levels in the y direction. The 256 levels represent an increasing scale of discrete voltages, and each data point is placed at the level which most nearly corresponds to the actual voltage level of the analog signal at that sampled location. The resulting digital signal comprises 2,048 data points, and it closely approximates the analog signal. The digital signal with a few representative data points 44 is shown in FIG. 2b.

The digital signal is then received by the interface unit 22, which passes the unaltered digital word to the buffer memory unit 26 of the tape recorder 24. As soon as the signal is sent to the buffer memory unit 26, interface unit 22 sends a control signal back to amplifier 18. This control signal enables the amplifier 18, which then sends the next reflected pulse signal to the analog-to-digital converter 20.

The digital signal from interface unit 22 is received by the buffer memory unit 26 of the tape recorder 24. The buffer memory unit 26 feeds the signal to the format control unit 28. Both the buffer memory unit 26 and the format control unit 28 adjust the signal so that it is compatible with the elements of the recording head 30, which then records the signal on magnetic tape. A single tape contains a large number of such recorded signals in groups. The number of signals in a group is variable. Because the pulses have a short duration (less than 4 microseconds), the frequency of the pulses is made proportional to the rate of flow in order to prevent any particle in the flow from passing through the conduit between consecutive pulses. Preferably, a group of twenty-four signals is used with an average flow rate. However, it is desirable to use larger or smaller groups, respectively, for faster or slower flow rates.

Not every pulse is reflected from a discontinuity in the flow, and, therefore, some of the signals in a given group may contain no discontinuity information. Other signals in the same group may contain duplicate particle information as successive pulses from the transmitter-receiver may be reflected from the same discontinuity.

The tape is then fed to the computer 32. The computer 32 is programmed with the BIGJOB program of Micro Pure, Inc., and the visual graphics terminal 34 displays in a grid formation the various program options which can be selected. Selection is made by touching the light pen 36 to the appropriate grid. Initially, the word select function is chosen, and the first signal in the group on the tape is displayed on the terminal 34. If the signal displayed does not contain any discontinuity information, the skip function is selected, and the next signal in the group is displayed. The signals of the tape are successively displayed on the terminal until a signal with discontinuity information is found. FIG. 2c shows the display on the terminal 34 for a signal containing discontinuity information.

The select information function is then activated, and as shown in FIG. 2c, the light pen 36 is used to bracket the portion of the signal representing the reflected pulse from the discontinuity. The computer is then instructed to perform a fast Fourier transform on this bracketed portion of the signal. This portion of the computer program is the Digital Systems FFT Subroutine Program (Version 3). The result is a frequency spectrum for the discontinuity. A frequency spectrum is essentially a plot of peak magnitudes on a positive and negative frequency scale, and the spectra of various discontinuities are quite distinct. For example, FIG. 2d is a frequency spectrum for an air bubble, and FIG. 2e is a frequency spectrum for a polystyrene particle.

The frequency spectrum for the unknown discontinuity is then displayed on the terminal 34 and compared with the frequency spectra of known discontinuities. When an identical frequency spectrum is found, the unknown discontinuity is identified. In addition to the display of the spectrum on the terminal, the spectrum may be stored on a disc or printed out on a printer (both disc and printer not shown) for future reference.

What is claimed is:

1. A method of identifying and distinguishing different types of discontinuities in a flow comprising:
   directing a transmitted pulse of short duration and rich in frequency components essentially transversely across the flow,
   detecting an ultrasonic pulse reflected from an unknown discontinuity in the flow, which reflected pulse need not have any frequency change due to discontinuity movement,
   transforming said reflected pulse into a multi-component frequency spectrum, in which certain of the frequency components of said reflected pulse are enhanced because of the type of discontinuity reflecting said pulse, and
   comparing said frequency spectrum with the frequency spectra of known discontinuities, in which spectra different frequency components are enhanced, until a matching frequency spectrum is found.

2. The method of claim 1 wherein said transforming initially comprises converting said pulse to a digital signal.

3. The method of claim 2 wherein said transforming further comprises performing a fast Fourier transform on said signal.

4. The method of claim 1 further comprising selecting a portion of said pulse representing said unknown discontinuity and transforming only said selected portion of said pulse.

5. An apparatus for identifying and distinguishing different types of discontinuities in a flow, comprising,
   means for transmitting an ultrasonic pulse of short duration and rich in frequency components essentially transversely across a flow containing unknown discontinuities,
   means for receiving a reflected ultrasonic pulse from an unknown discontinuity, which reflected pulse need not have any frequency change due to discontinuity movement,
   means for transforming said reflected pulse into a multi-component frequency spectrum, in which certain of the frequency components of said reflected pulse are enhanced because of the type of discontinuity reflecting said pulse,
   means for displaying said frequency spectrum, and
   means for comparing said frequency spectrum with the frequency spectra of known discontinuities, in which spectra different frequency components are enhanced, until a matching frequency spectrum is found.

6. The discontinuity identification apparatus of claim 5 wherein said means for transforming comprises an analog-to-digital converter which converts said reflected pulse into a digital signal.

7. The discontinuity identification apparatus of claim 5 wherein said means for displaying comprises a visual graphics terminal.

* * * * *